US00PP29366P2

(12) United States Plant Patent
Zaiger et al.

(10) Patent No.: US PP29,366 P2
(45) Date of Patent: Jun. 12, 2018

(54) INTERSPECIFIC TREE NAMED 'FLAVOR MIST'

(50) Latin Name: ***Interspecific Prunus* species**
Varietal Denomination: Flavor Mist

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 52 days.

(21) Appl. No.: 15/530,117

(22) Filed: Dec. 5, 2016

(51) Int. Cl.
*A01H 5/08* (2018.01)

(52) U.S. Cl.
USPC ..... Plt./180
CPC ..... *A01H 5/0837* (2013.01)

(58) Field of Classification Search
USPC ..... Plt./180
See application file for complete search history.

*Primary Examiner* — Anne Marie Grunberg

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree with vigorous, upright growth.
2. Heavy and regular bearer of large size, yellow flesh fruit.
3. Fruit with an attractive dark purple skin color.
4. Fruit with good flavor and eating quality.
5. Fruit with good storage and shipping ability.

1 Drawing Sheet

Botanical designation: Interspecific *Prunus* species.
Variety denomination: 'Flavor Mist'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of interspecific and plum trees, which are known to us, and mentioned herein, 'Coparose' Interspecific (U.S. Plant Pat. No. 20,173), the proprietary non-patented interspecific seedlings '340LU282', '66Z352', '31Z635', '121LT36', '31Z1061' and the proprietary non-patented plum seedling '93LG577'.

STATEMENT REGARDING FEDERALLY SPONSORED RESEARCH AND DEVELOPMENT

Not applicable.

ORIGIN OF THE VARIETY

The new and distinct variety of interspecific tree was developed by us in our experimental orchard located near Modesto, Calif. as a first generation cross between our proprietary non-patented interspecific seedling selections '340LU282' and '121LT36'. The seed parent (340LU282) originated from crosses between our non-patented interspecific seedling selections '66Z352' and '31Z635'. The pollen parent (121LT36) originated from crosses between the proprietary non-patented plum seedling '93LG577' and the proprietary non-patented interspecific seedling '31Z1061'. A large number of these first generation seedlings were budded onto older established trees of 'Nemaguard' Rootstock (non-patented) to accelerate rapid fruit production. Under close and careful observation, we recognized the desirable tree and fruit characteristics of the present seedling and selected it in 2008 for additional asexual propagation and commercialization.

ASEXUAL REPRODUCTION OF THE VARIETY

In 2008 asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new and distinct variety of interspecific tree is of large size, vigorous, upright growth and a regular and productive bearer of large size, clingstone fruit with an attractive dark purple skin color. The fruit is further characterized by its firm, yellow flesh, good flavor and eating quality with good handling and shipping ability. In comparison to its non-patented interspecific seed parent (340LU282) the fruit of the new variety is larger in size and has better eating quality. In comparison to its non-patented interspecific pollen parent (121LT36) the fruit of the new variety is approximately 38 days earlier in maturity and has dark purple skin compared to red. In comparison to the commercial variety 'Coparose' Interspecific (U.S. Plant Pat. No. 20,173) the fruit of the new variety has dark purple skin compared to light red and is larger in size.

DESCRIPTION OF THE PHOTOGRAPH

The accompanying color photographic illustration shows typical specimens of the foliage and fruit of the present new interspecific variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 8 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 8 year old specimens grown near Modesto, Calif., with color in accordance with Munsell Book of Color published in 1958.

Tree:

*Size*.—Large, pruned to 3 to 3.5 meters in height and width for economical harvesting of fruit. Size varies with different cultural practices.

*Vigor*.—Vigorous, tree growth of approximately 1.5 to 2 meters the first growing season. Varies with cultural practices, soil type, fertility and climatic conditions.

*Form*.—Upright, usually pruned to vase shape.

*Branching habit*.—Upright, crotch angle approximately 30°, increases with heavy crop load.

*Productivity*.—Productive, thinning and spacing of fruit necessary for desired market size. Fruit set varies with climatic conditions during bloom time.

*Bearer*.—Regular, adequate fruit set 6 consecutive years. No alternate bearing observed.

*Fertility*.—Self-sterile, pollinator required.

*Density*.—Medium dense, usually pruned to vase shape to increase sunlight and air movement to center of tree to enhance fruit quality and health of fruit spurs.

*Hardiness*.—Hardy in all stone fruit growing areas of California. Tree grown in USDA Hardiness Zone 9. Winter chilling requirement approximately 800 hours at or below 45° F.

Trunk:

*Size*.—Large. Average circumference 53.3 cm at 25.4 cm above ground on a 8 year old tree.

*Stocky*.—Medium stocky.

*Texture*.—Medium shaggy, roughness increases with age.

*Color*.—Varies from 2.5GY 4/2 to 2.5GY 2/2.

Branches:

*Size*.—Medium. Average circumference 16.5 cm at 1.2 meters above ground. Crotch angle approximately 30°, increases with heavy crop load.

*Surface texture*.—New growth relatively smooth. Mature growth medium rough, roughness increases with age.

*Lenticels*.—Average number 74 in a 25.8 square cm area. Average length 4.5 mm. Average width 1.2 mm. Color 10YR 5/6.

*Color*.—New growth varies from 5GY 7/6 to 5GY 6/6. Mature growth varies from 5YR 3/4 to 5YR 2/4, varies with age of growth.

Leaves:

*Size*.—Small to medium. Average length 80.3 mm. Average width 37.0 mm.

*Form*.—Elliptical.

*Apex*.—Acuminate.

*Base*.—Cuneate.

*Margin*.—Doubly serrate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Average length 10.7 mm. Average width 1.2 mm. Longitudinally grooved. Surface — glabrous. Color varies from 5GY 8/6 to 5GY 7/6.

*Glands*.—Type — globose. Size — small. Average length 0.5 mm. Average diameter 0.5 mm. Number varies from 1 to 2, average number 2. Located primarily on the base of leaf blade and upper portion of petiole. Color 5R 3/4.

*Stipules*.—Average number 2. Average length 5.2 mm. Edges — pectinate. Color varies from 5GY 8/6 to 5R 3/4.

*Color*.—Upper surface varies from 2.5GY 3/4 to 5GY 4/4. Lower surface varies from 2.5GY 5/4 to 5GY 5/4. Midvein color varies from 7.5Y 7/6 to 10Y 8/6.

Flower buds:

*Size*.—Medium. Average length 10.0 mm. Average diameter 6.8 mm.

*Hardiness*.—Hardy with respect to California winters.

*Density*.—Dense.

*Form*.—Conical, becoming elongated just before opening.

*Pedicel*.—Average length 7.9 mm. Average width 0.6 mm. Surface — glabrous. Color 2.5GY 7/6.

*Color*.—N 9.5/(white).

*Number of buds per spur*.—Average number 7, varies from 6 to 9.

Flowers:

*Blooming period*.—Date of First Bloom Feb. 8, 2016. Date of Petal Fall Feb. 18, 2016, varies slightly with climatic conditions.

*Size*.—Medium. Average height 10.4 mm. Average diameter 16.8 mm.

*Petals*.—Normally 5, alternately arranged to sepals. Size — medium to large. Average length 10.8 mm. Average width 9.6 mm. Form — elliptical. Arrangement — overlapping. Petal apex — rounded. Petal base — truncate. Margin — sinuate. Color N 9.5/(white). Both upper and lower surfaces glabrous.

*Sepals*.—Normally 5, alternately arranged to petals. Size — medium. Average length 3.3 mm. Average width 3.4 mm. Shape — triangular. Apex — triangular. Margin — entire. Both upper and lower surfaces glabrous. Color — upper surface 10Y 7/10. Lower surface 2.5GY 6/6.

*Stamens*.—Average number per flower 27. On average, the stamens are above the height of the petals. Average filament length 8.0 mm. Filament color N 9.5/(white). Anther color varies from 7.5R 4/10 to 5Y 8.5/10.

*Pollen*.—Self sterile, pollinator required. Color 2.5YR 4/10.

*Pistil*.—Number — normally 1. Average length 8.1 mm. Position of stigma an average of 1.9 mm below anthers. Surface — glabrous. Color 2.5GY 8/6.

*Fragrance*.—Slight.

*Color*.—N 9.5/(white).

*Pedicel*.—Average length 7.0 mm. Average width 0.7 mm. Surface — glabrous. Color 2.5GY 7/6.

*Number flowers per flower bud*.—Average 2, varies from 1 to 3.

Fruit:

*Maturity when described*.—Firm ripe and ready for consumption.

*Date of first picking*.—Jul. 3, 2016.

*Date of last picking*.—Jul. 13, 2016, varies slightly with climatic conditions.

*Size*.—Large. Average diameter axially 57.9 mm. Average transversely in suture plane 69.5 mm. Average weight 176.1 grams, varies slightly with fertility of the soil, amount of thinning and climatic conditions.

*Form*.—Globose.

*Suture*.—Lipped.

*Ventral surface*.—Lipped.

*Apex*.—Slightly retuse.

*Base*.—Flat.

*Stem cavity*.—Rounded to slightly elongated in suture plane. Average depth 8.0 mm. Average diameter 5.6 mm.

Stem:

*Size*.—Large. Average length 16.9 mm. Average diameter 2.0 mm.

*Color*.—Varies from 2.5GY 5/6 to 5YR 4/6.

Flesh:

*Ripens*.—Evenly.

*Texture*.—Firm, meaty.

*Fibers*.—Few, small, tender.

*Firmness*.—Firm, comparable to other commercial interspecific varieties.

*Aroma*.—Moderate.

*Amydgalin*.—Undetected.

*Eating quality*.—Good.

*Flavor*.—Good, having a good balance between acid and sugar.

*Juice*.—Heavy amount, enhances flavor.

*Acidity*.—Not available.

*Brix*.—Average Brix 18.5°, varies slightly with amount of fruit per tree and climatic conditions.

*Pit cavity*.—Average length 24.7 mm. Average width 21.2 mm. Average depth 6.8 mm. Color varies from 2.5Y 7/8 to 5Y 7/6.

*Color*.—Varies from 5Y 8.5/6 to 5Y 8/8.

Skin:

*Thickness*.—Medium.

*Surface*.—Smooth.

*Bloom*.—Moderate amount, complete coverage.

*Tendency to crack*.—None.

*Color*.—Ground color varies from 2.Y 8.5/4 to 5Y 8/6. Overspread with 7.5R 2/2 to 10R 2/4.

*Tenacity*.—Tenacious to flesh.

*Astringency*.—Undetected.

Stone:

*Type*.—Clingstone, strong adherence to flesh.

*Size*.—Large. Average length 24.2 mm. Average width 20.7 mm. Average thickness 12.5 mm.

*Form*.—Ovoid.

*Base*.—Flat.

*Apex*.—Rounded.

*Surface*.—Slightly pitted throughout. One shallow groove on each side of suture extending from base to apex.

*Sides*.—Unequal, one side extending further outward from suture plane.

*Ridges*.—Small, extending from base toward apex.

*Tendency to split*.—None.

*Color*.—Varies from 10YR 5/8 to 7.5YR 4/8 when dry.

Kernel:

*Size*.—Medium. Average length 13.4 mm. Average width 10.4 mm. Average depth 5.7 mm.

*Form*.—Ovate.

*Viability*.—Viable, complete embryo development.

*Skin color*.—Varies from 5Y 9/6 to 5Y 8.5/4.

Use:

*Dessert*.—Market — local and long distance.

Keeping quality: Good, held firm 3 weeks at 38° to 42° F. without internal breakdown of flesh or appreciable loss of flavor.

Shipping quality: Good, minimal skin scarring or bruising of flesh during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program. No atypical resistances/susceptibilities have been noted under normal cultural practices. The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

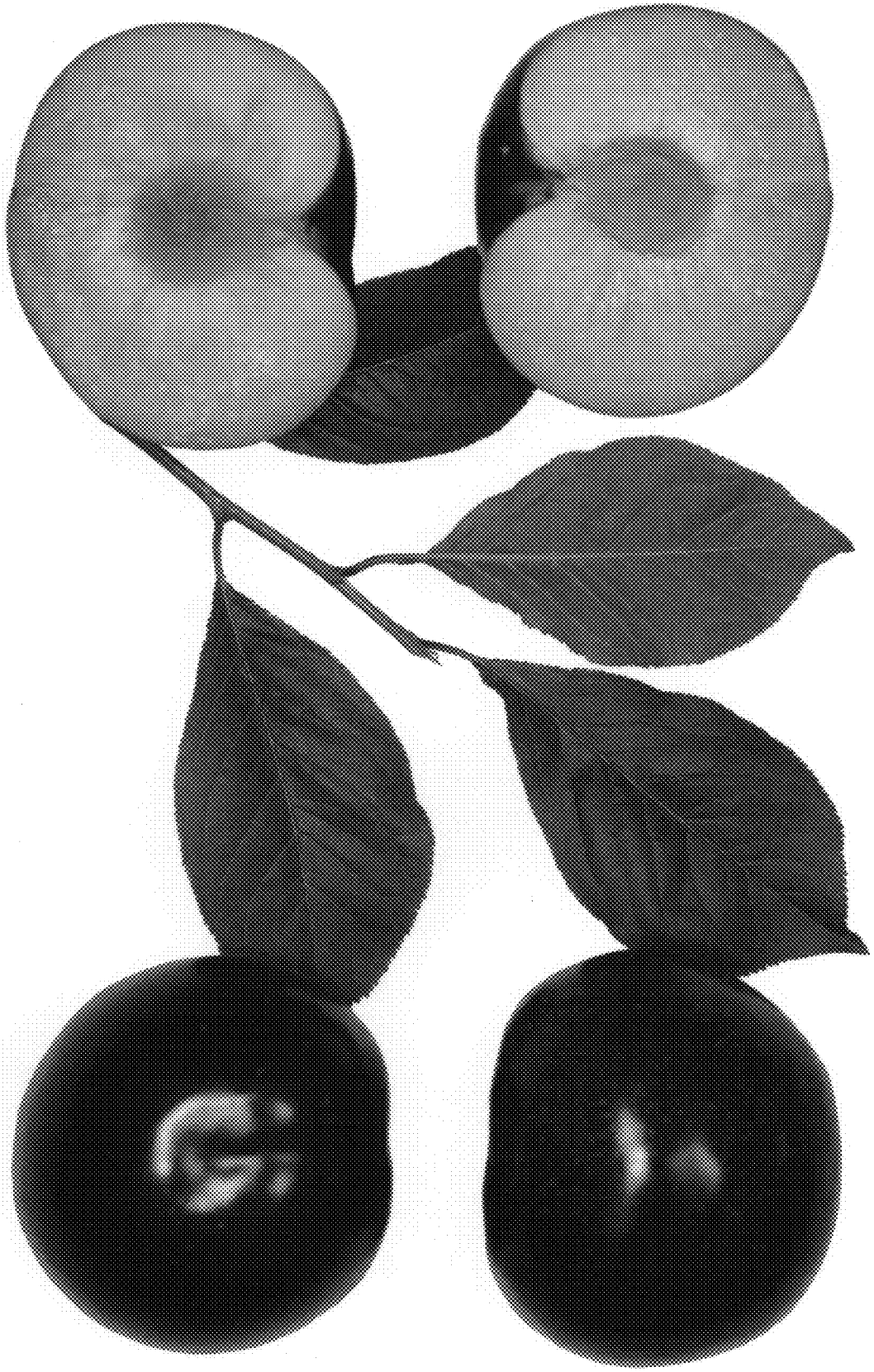

* * * * *